United States Patent
Hsieh et al.

(10) Patent No.: US 10,130,654 B2
(45) Date of Patent: Nov. 20, 2018

(54) METHOD OF INDUCING OSTEOGENSIS AND PROMOTING OSSEOINTEGRATION AROUND AN IMPLANT

(71) Applicant: HANGLI BIOSCIENCES CO., LTD., New Taipei (TW)

(72) Inventors: Yao Dung Hsieh, Kaohsiung (TW); Earl Fu, Taipei (TW); Su Fang Kung, New Taipei (TW); E-Chin Shen, Taipei (TW)

(73) Assignee: HANGLI BIOSCIENCES CO., LTD., New Taipei (TW)

(*) Notice: Subject to any disclaimer, the term of this patent is extended or adjusted under 35 U.S.C. 154(b) by 460 days.

(21) Appl. No.: 14/735,502

(22) Filed: Jun. 10, 2015

(65) Prior Publication Data

US 2015/0272983 A1    Oct. 1, 2015

Related U.S. Application Data

(63) Continuation-in-part of application No. 13/295,306, filed on Nov. 14, 2011, now abandoned.

(30) Foreign Application Priority Data

May 24, 2011 (TW) .............................. 100118163 A

(51) Int. Cl.
| | | |
|---|---|---|
| *A61K 31/722* | (2006.01) | |
| *A61K 38/18* | (2006.01) | |
| *A61K 45/06* | (2006.01) | |
| *A61K 9/00* | (2006.01) | |
| *A61K 38/00* | (2006.01) | |

(52) U.S. Cl.
CPC .......... *A61K 31/722* (2013.01); *A61K 9/0024* (2013.01); *A61K 38/1808* (2013.01); *A61K 45/06* (2013.01)

(58) Field of Classification Search
CPC ................. A61K 31/722; A61K 9/5161; A61K 47/6939; A61K 47/6935
See application file for complete search history.

(56) References Cited

U.S. PATENT DOCUMENTS

| | | | | |
|---|---|---|---|---|
| 2003/0203003 A1* | 10/2003 | Nelson | ..................... | A61K 9/70 424/426 |
| 2005/0226905 A1* | 10/2005 | Tien | ..................... | A61K 9/0024 424/439 |
| 2008/0118542 A1* | 5/2008 | Arnander | ............. | A61K 31/715 424/423 |
| 2009/0004276 A1* | 1/2009 | Ben-Shalom | .......... | A61K 8/042 514/1.1 |
| 2009/0281058 A1* | 11/2009 | Gislason | ................. | A61L 24/08 514/55 |
| 2011/0124717 A1* | 5/2011 | O'Connor | ............ | A61K 31/405 514/44 R |
| 2013/0287856 A1* | 10/2013 | Caprasse | .............. | A61K 9/5031 424/490 |
| 2014/0199327 A1* | 7/2014 | Dixit | .................. | G01N 33/5011 424/158.1 |

OTHER PUBLICATIONS

Yang et al. (2010) Effects of chitosan/collagen substrates on the behavior of rat neural stem cells, Lif Sci., vol. 53, pp. 215-222.*
Olteanu et al. (2007) Chitosan involved Tissue Engineering and Regenerative Medicine, pp. 1-16.*
Silva et al. (2001) On the piezoelectricity of collagen-chitosan films, Phys. Chem. Chem. Phys., vol. 3, pp. 4154-4157.*
Mathew et al. (2011) A novel tripolymer coating demonstrating the synergistic effect of chitosan, collagen type 1 and hyaluronic acid on osteogenic differentiation of human bone marrow derived mesenchymal stem cells, Biochem. Biophys. Res., vol. 414, pp. 270-276.*

* cited by examiner

*Primary Examiner* — Manjunath N Rao
*Assistant Examiner* — Samuel W Liu
(74) *Attorney, Agent, or Firm* — WPAT, PC

(57) ABSTRACT

The invention relates to a method of inducing osteogenesis in a subject comprising administrating a chitosan material to the a subject in need of osteogenesis, wherein the chitosan material having a chitosan with a degree of deacetylation at the range of 70%~90%, and the chitosan is 0.15% by weight of the chitosan material. The method of the present invention can induce bone-forming and promote osseointegration around an implant.

2 Claims, 5 Drawing Sheets
(5 of 5 Drawing Sheet(s) Filed in Color)

METHOD OF INDUCING OSTEOGENSIS AND PROMOTING OSSEOINTEGRATION AROUND AN IMPLANT

CROSS-REFERENCES TO RELATED APPLICATIONS

This is a continuation-in-part of U.S. application Ser. No. 13/295,306, filed on Nov. 14, 2011, which is incorporated herewith by reference.

BACKGROUND OF THE INVENTION

1. Field of the Invention

The present invention relates to a method of inducing osteogenesis, in particular to a method of inducing bone-forming and promoting osseointegration around a titanium implant surface.

2. The Prior Arts

The osteoconduction of a bone graft indicates that the bone graft is provided as a support in a bone defect area, and osteoprogenitor cells are allowed to scramble on the graft and then converted via proliferation and differentiation into osteoblast cells by which the osteogenesis can take place, whereas the osteoinduction means that the bone graft is able to induce mesenchymal cells around it or bone marrow stem cells from the blood to differentiate into osteoprogenitor cells.

The best material for a bone graft is an autologous bone graft that is obtained from the own body, the advantages of which include that cell activity may last during its implantation and there is no problem with disease infection. However, due to limited available quantities of the autologous bone grafts as well as possible pains and bleeding after operation, researchers sought for years to find an another excellent bone graft to recover its defects. In this regard, it is proposed to implant an improved demineralized bovine bone graft into murine muscles to induce osteogenesis. Afterwards, a number of studies are focused on the application of demineralized freeze-dried bone allografts in the treatment of periodontal defect and results from the studies also demonstrate it exactly has an effect of promoting bone formation.

Demineralized freeze-dried bone allografts can be employed in the treatment of bone defects to promote the bone formation, but they may contain proteins remaining in the bone grafts, the proteins can become antigens of an immune response, and can be contaminated by microorganisms, for example, mad cow disease. Therefore, it is of great importance to find a substitute that can be used to replace allografts to induce osteogenesis and therefore treat the bone defects.

It is known that chitosan is an essential complicated polysaccharide that is obtained by deacetylating chitin at high temperature and in the concentrated acidic and basic solutions. Chitin is a naturally occurring polysaccharide next to cellulose and widely spread in animals and plants. Previous studies have shown that chitosan can be used to promote cells to adhere and grow, or used as carrier of delivering drugs. However, as a result of extraordinarily rapid degradation and high expansion rate of chitosan membrane, a short life span is the problem of the wrapping material out of chitosan membrane.

SUMMARY OF THE INVENTION

To solve the problems existing in the prior art, an objective of the present invention is to provide a method of inducing osteogenesis by using a chitosan material, and the chitosan material is a good biocompatibility in order to avoid the immune response in bodies that is caused by the bone graft.

Another objective of the present invention is to provide a method for promoting osteointegration around an implant.

Another objective of the present invention is to provide a method of treating bone defects in a subject.

The chitosan material of the present invention for induction of osteogenesis around an implant, comprising a chitosan having a degree of deacetylation at the range of 70%~90%. The chitosan material further comprises a pharmacologically acceptable carrier, such as a collagen, and in addition an antibacterial agent, a local anaesthetic, an epithelial growth factor or any combination thereof. Treatment of the bone defects with the chitosan material of the present invention can induce the regeneration of bone cells around the bone defects and the bone is repaired in this way.

As a result of the excellent biocompatibility of chitosan, namely no immune response in contact with living cells, it is extensively used as biomedical materials with biocompatibility. In one embodiment, the collagen of the chitosan material of the present invention is present in the form of a thin membrane and the chitosan is absorbed in the collagen membrane. Treatment of bone cell regeneration in mammalians with the method of the present invention does not also give rise to the possible immune response in animals caused by the known bone graft. Furthermore, both chitosan and collagen are easily obtained; therefore the chitosan material made out of them can substantially lower the cost of the bone defect repair.

The present invention will be explained in more details, based on the following embodiments. The embodiments stated in the text do not limit the abovementioned disclosure of the present invention. Those skilled in the art may do some improvements and modifications without departing from the scope of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1B refers to a 750 kDa chitosan-collagen composition test group.

DETAILED DESCRIPTION OF THE PREFERRED EMBODIMENT

Figure 1A:
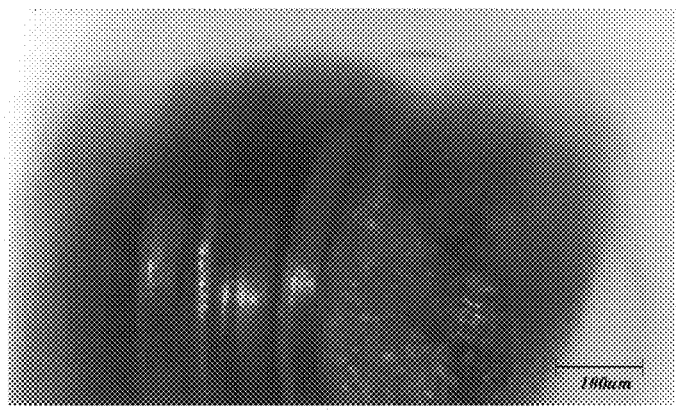
FIGS. 1A and 1B show experimental group with positive whole mount staining (red color) of a calcified tissue on the implant surfaces, wherein FIG. 1A refers to a 450 kDa chitosan-collagen composition test group.

The term "about" used in the present invention indicates a value range of ±5%.

The method of the present invention for induction of osteogenesis by using a chitosan material, wherein the chitosan material comprises a chitosan having a degree of deacetylation at the range of 70%~90%. To facilitate the implementation of the method of the present invention, the chitosan material further comprises a pharmacologically acceptable carrier. The pharmacologically acceptable carrier is not particularly limited; any known carriers that can be used in a pharmaceutical composition can be used in the present invention, such as collagen. In addition, the chitosan material of the present invention further comprises an antibacterial agent, a local anesthetic, an epithelial growth factor or any combination thereof.

The chitosan of the present invention is not particularly limited. Based on the definition known for chitosan, it usually has a structural formula as shown in the following formula I:

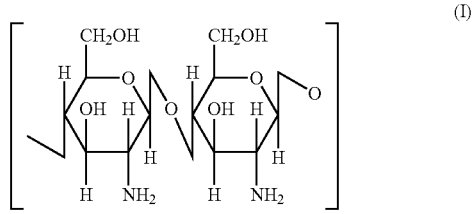

Furthermore, the chitosan of the present invention can be prepared for example by deacetylating chitin. Based on the definition known for chitosan, it usually has a structural formula as shown in the following formula II:

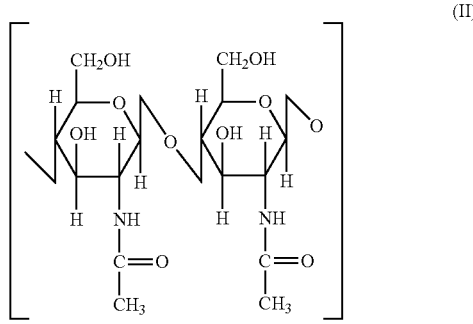

The deacetylation degree of the above chitosan used in the present invention is not particularly limited. In view of the known definition for the deacetylation degree of chitosan, the deacetylation degree of chitosan is preferably more than 70%, more preferably more than 80%, the most preferably more than 90%.

The known chitosan is a high molecular polymer that usually has a molecular weight of more than ten thousands daltons. The molecular weight of chitosan in the present invention is preferably from 5 kDa to 1,000 kDa, more preferably from 100 kDa to 1,000 kDa.

The chitosan is 0.15% by weight of the chitosan material of the present invention. In a preferred embodiment of the present invention, the collagen is present in the form of a thin membrane as a pharmacologically acceptable carrier and the chitosan is absorbed in the collagen membrane. The present invention also provides a method for promoting osseointegration by using the chitosan material, wherein the chitosan material is a wrap around the surface of an implant into a subject body, and the subject is a mammalian.

Besides the ability to effectively induce bone cell formation, the method of the present invention has good biocompatibility and does not cause undesired immune responses in organisms when in use. This reveals the method of the present invention is extremely suitable for the induction of osteogenesis and thus for the treatment of bone defects.

Embodiment 1

Take a small pure titanium implant and wrap its surface with a type-I collagen membrane by a known method.

Chitosan (Primex Ingredients AS, Avaldenes, Norway) with molecular weight, 450 kDa and 750 kDa, and with deacetylation degree, more than 90%, was used for test. A vitamine C solution, 20 mg/mL, was prepared in deionized water. 15 mg of chitosan powder were then added to 10 mL of the vitamine C solution to prepare a 0.15% chitosan solution. A type-I collagen membrane (BioMend®, Integra Life Sciences, Carlsbad, Calif., USA), 3 mm×5 mm, was subsequently soaked in 10 mL of the foregoing chitosan solution, so that the chitosan molecules were absorbed in the type-I collagen membrane. The type-I collagen membrane is then used to wrap a small pure titanium implant (1.6 mm diameter and 3 mm length; Biodent, Tokyo, Japan). In this way, a small pure titanium implant, the surface of which was wrapped with a type-I collagen membrane, in which the chitosan molecules had been already absorbed, was prepared.

Each test group included 15 implants wrapped with a type-I collagen membrane, in which either 450 kDa or 750 kDa chitosan had been absorbed. The negative control group consisted of 15 implants wrapped with a type-I collagen membrane that had been wet with the vitamine C solution.

Fifteen 5-week-old Sprague-Dawley male rats were used for the test. These small pure titanium implants of the test group and the negative control group were respectively inserted into the subcutaneous region on the back of the rats, wherein the narcosis was carried out by using intramuscular injection of a combination of fentanyl citrate (0.315 mg/mL) and fluanisone (10 mg/mL) at a dose of 0.01 mL/100 g body weight. Five rats were then randomly selected from the 15 rats for whole mount staining for the purpose of preliminary identification of the new bone formation.

Figure 1B:
Figure 1C:
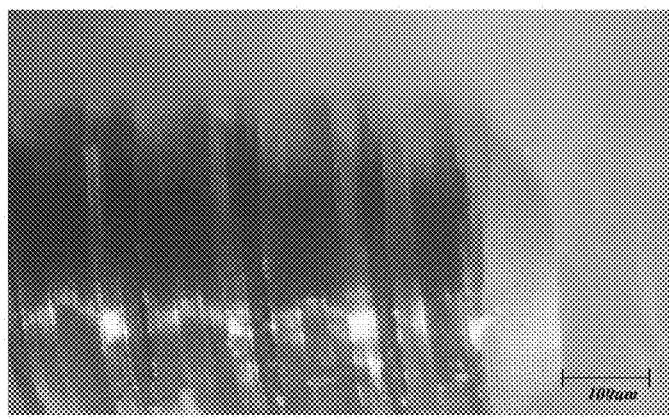
FIG. 1C refers to a control group with negative whole mount staining on the implant surface wrapped with type-I collagen membrane; the staining is carried out with Alizarin red and the original magnification is at ×50.

The surrounding tissues around the implants were obtained from the five rats and then were stained using whole mount staining. For the chitosan material of 450 kDa chitosan-collagen or 750 kDa chitosan-collagen, the test groups showed a strong Alizarin red staining, see FIGS. 1A and 1B. For the negative control group, where the surface of the implant was wrapped with a type-I collagen membrane, the surrounding tissues around the implants did not show any Alizarin red staining, see FIG. 1C. These results strongly suggested that there were calcified structure in the chitosan-collagen test groups. However, Alcian blue staining showed no chondrogenesis in both chitosan-collagen composition test groups and the negative control group. The fractions of samples from the surfaces of implants showing positive staining results in each group were listed in Table 1.

TABLE 1

| Group | Fraction of smaples showing positive staining results (positive staining/total) | |
|---|---|---|
| | Alizarin red | Alcian blue |
| negative control | 0/5 | 0/5 |
| 450 kDa chitosan-collagen | 5/5 | 0/5 |
| 750 kDa chitosan-collagen | 5/5 | 0/5 |

Six weeks after implant insertion, all rats were killed and the implants and surrounding tissues were removed. Alizarin red and Alcian blue were used to observe the tissues resulted from chondrogenesis and osteogenesis around the surface of the pure titanium implants in the four groups. Once a bony structure in the chitosan-collagen composition test groups was identified by whole mount staining, a further histomorphological verification of the newly induced bone was carried out against the other 10 rats.

On the first day and the fourth day before the rats were killed, the rats were injected with Alizarin red (0.2 mg/100 g body weight) and Calcein (0.3 mg/100 g body weight, fluorescent dye). The implants were removed and tissue sections from the surface of the implants were performed. Osteopontin and alkaline phosphatase in the tissue sections were subsequently stained using Toluidine blue (TB), Masson-Goldner Trichrome or immunohistochemistry stain (IHC stain) to evaluate the bone formation. After these samples had been further processed, they were incubated with primary antibody, i.e. anti-osteopontin antibody or anti-alkaline phosphatase antibody at 4° C. over night. The titers of these antibodies had been checked and the final dilutions were 1:200 and 1:1000, respectively. The primary antibody in the negative control group was replaced by bovine serum albumin (BSA).

After the two test groups of the chitosan-collagen compositions, 450 kDa or 750 kDa, had been qualitatively analyzed, histomorphometric analyses were further carried out using microscope at ×200 magnification to quantitatively compare the osseoinductive ability for the following parameters: (i) trabecular bone surface, measured by counting the number of cutting points; a cutting point is the area of trabecular surface per unit volume of bone tissue, Sv in $mm^2/mm^3$; (ii) trabecular bone volume, measured by counting the number of hits; a hit is the volume occupied by trabecular bone expressed as a fraction of the volume occupied by bone marrow plus trabecular bone, BV/TV in $mm^3/mm^3$; and (iii) mean wall thickness, determined by measuring the mean thickness of new bone formed at bone-forming sites when the formation phase was complete, or the mean distance between cement lines and the trabecular surfaces of completed structural units, MWT in μm.

The results from the collagen negative control group showed a negative response. The nature of the calcified structures in the test groups was investigated using histomorphological approaches, including Toluidine blue stain, Masson-Goldner trichrome stain and immunohistochemical staining with osteopontin and alkaline phosphatase.

Figure 2A:
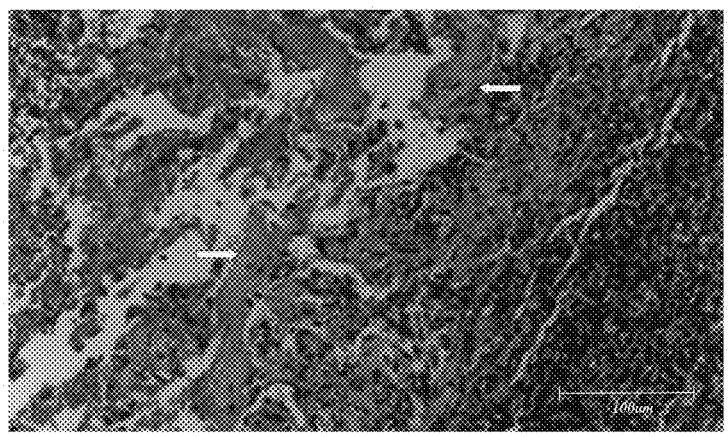
FIGS. 2A and C are magnified at ×100, FIGS. 2B and D at ×400, FIGS. 2E and F at ×40).
Figure 2B:
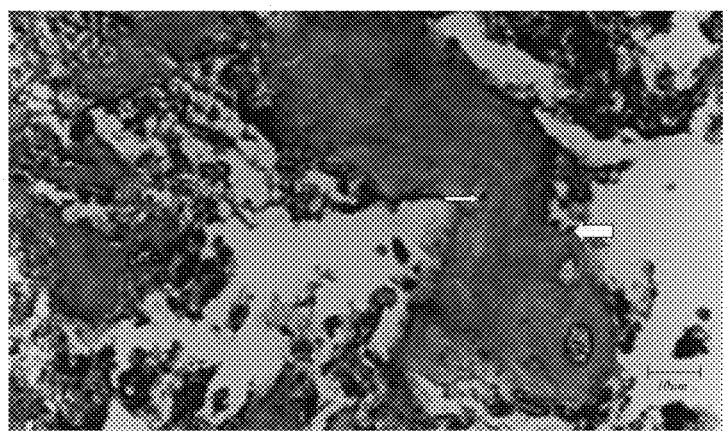
FIG. 2B higher magnification view of section shown in FIG. 2A illustrates the osteocytes (thin arrow) laid within the calcified bone and osteoblasts (thick arrow) aligned on the bone surface.
Figure 2C:
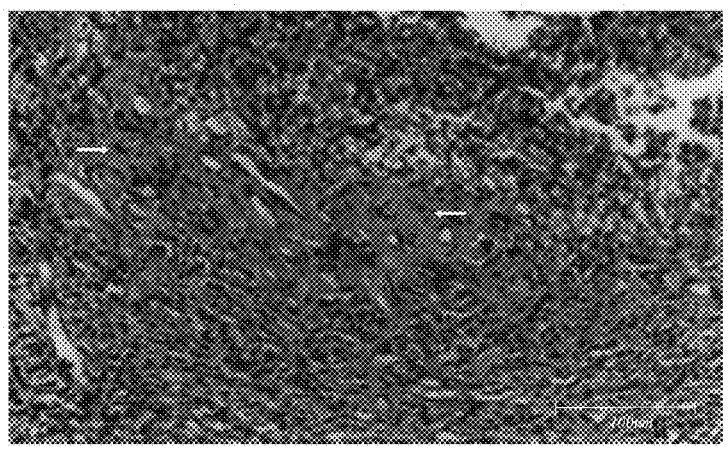
FIG. 2C tissue section from a 750 kDa test group showing calcified structures (arrows)
Figure 2D:
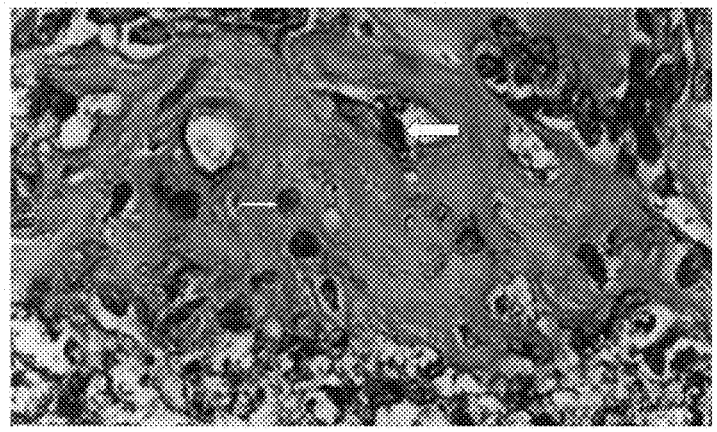
FIG. 2D higher magnification view of section shown in FIG. 2C illustrates the osteocytes (thin arrow) laid within the calcified bone and osteoblasts (thick arrow) aligned on the bone surface; histological sections of the 450 kDa test group FIG. 2E and 750 kDa test group FIG. 2F show calcified bony structure (stained blue) formed within surrounding connective tissue (FIGS. 2A-D, Toluidine blue stain.
Figure 2E:
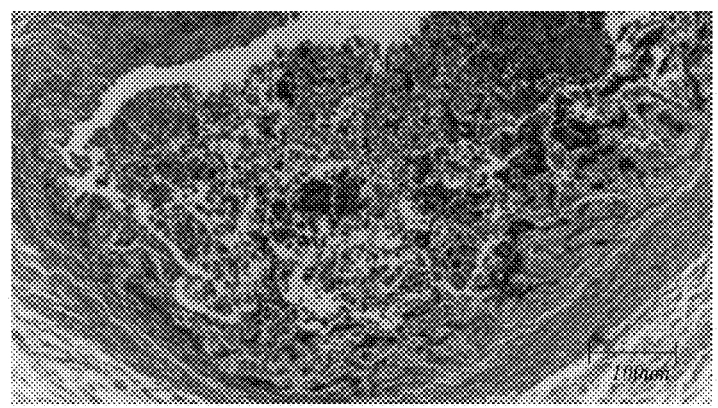
FIGS. 2E and F, Masson-Goldner trichrome stain; original magnification.
Figure 2F:
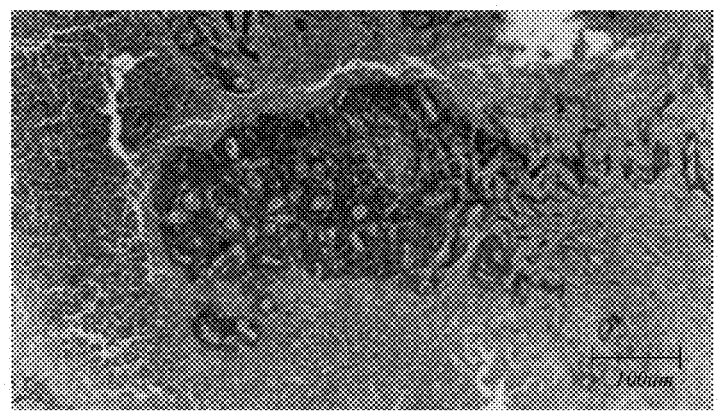
FIGS. 2 A to F show that bone formation was proved within connective tissues from all rats treated with both chitosan-collagen compositions, FIG. 2A tissue section from a 450 kDa test group showing calcified structures (arrows)

Bone formation was proved in tissues from all rats treated with both chitosan-collagen compositions. Toluidine blue staining on all tissue sections showed a bony structure with osteocytes trapped within calcified bone and osteoblasts aligned on the surfaces of calcified bone, as can be seen in the 450 kDa chitosan-collagen composition test group (see FIGS. 2A and 2B) and the 750 kDa chitosan-collagen composition test group (see FIGS. 2C and 2D). These bony structures were further confirmed by Masson-Goldner trichrome stain (blue), see FIGS. 2E and 2F.

Figure 3A:
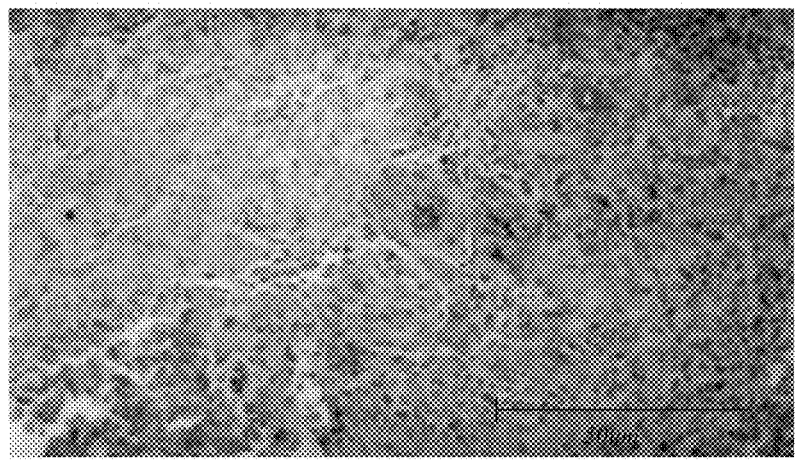
FIGS. 3A to 3D are a immunohistochemical staining of osteopontin showed strong positive staining (brown) widely distributed in FIG. 3A 450 kDa test group and FIG. 3B 750 kDa test group; immunohistochemical staining of alkaline phosphatase showed strong positive staining (orange) widely distributed in FIG. 3C 450 kDa test group and FIG. 3D 750 kDa test group; the original magnification is at ×200.
Figure 3B:
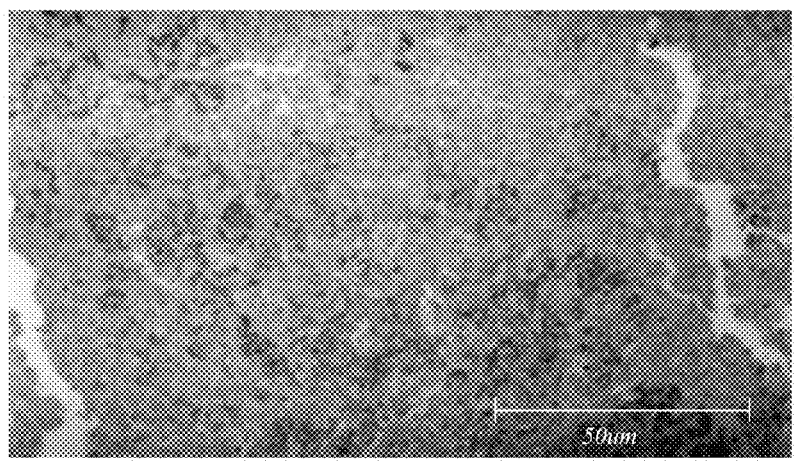
Figure 3C:
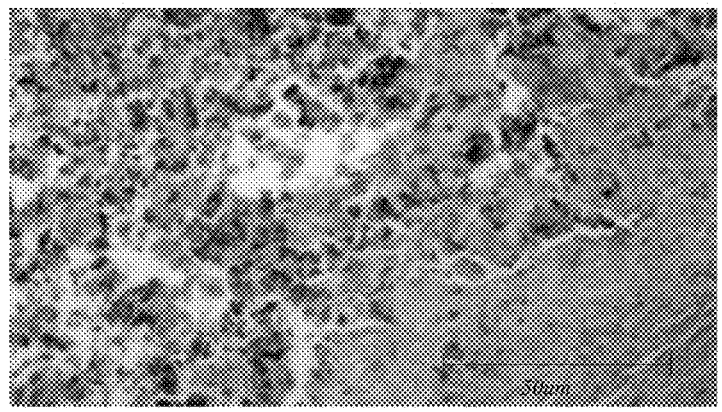
Figure 3D:
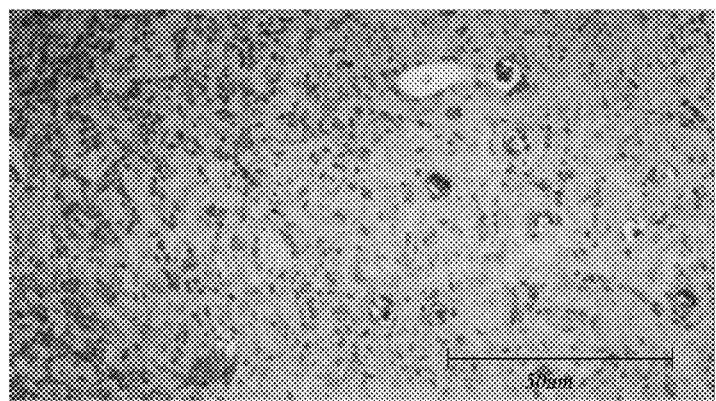

The expression of osteoblast-related proteins (osteopontin and alkaline phosphatase) was verified on the histologically observed new bone. The osteopontin staining indicated early bone formation activity, while alkaline phosphatase staining represented the calcification process of bone formation. The results from osteopontin staining showed a strong positive staining widely distributed in both the 450 kDa chitosan-collagen composition test group and the 750 kDa chitosan-collagen composition test group, see FIGS. 3A and 3B, respectively. Likewise, the results from alkaline phosphatase staining showed a strongly positive staining widely distributed in both the 450 kDa chitosan-collagen composition test group and the 750 kDa chitosan-collagen composition test group, see FIGS. 3C and 3D, respectively. The presence of the bone marker proteins (osteopontin and alkaline phosphatase) proved that the previously observed calcified structures were truly new bone.

After confirmation of bone formation in the 450 kDa and 750 kDa chitosan-collagen composition test groups by the histomorphological analysis, a quantitative evaluation was further carried out by histomorphometrical measurement of the trabecular bone surface (Sv, in $mm^2/mm^3$), trabecular bone volume (BV/TV, in $mm^3/mm^3$) and mean wall thickness (MWT, in μm). The results from histomorphometric analysis showed that the mean values of the three bone parameters in the 750 kDa chitosan-collagen composition test group were slightly higher than those in the 450 kDa chitosan-collagen composition test group. However, there were no statistically significant differences between these two groups in all parameters, including trabecular bone surface (Sv: 1.36±0.39 vs. 1.41±0.59 $mm^2/mm^3$), trabecular bone volume (BV/TV: 1.36±0.39 vs. 8.34±2.87 $mm^3/mm^3$) and mean (trabecular) wall thickness (MWT: 1.54±0.60 vs. 1.72±0.80 μm), see Table 2.

TABLE 2

Histomorphological analysis on the osteoinductive effect of the chitosan material of chitosan (with different molecular weights)-collagen compositions six weeks after implant insertion.

| | Molecular weight of chitosan | | |
|---|---|---|---|
| | 450 kDa | 750 kDa | p-value |
| Trabecular bone surface (Sv; $mm^2/mm^3$) | 1.36 (0.39) | 1.41 (0.59) | Not significant |
| Mean (trabecular) wall thickness (MWT; μm) | 7.87 (1.94) | 8.34 (2.87) | Not significant |
| Trabecular bone volume (BV/TV; $mm^3/mm^3$) | 1.54 (0.60) | 1.72 (0.80) | Not significant |

Student's paired t-test with a significant level of $p < 0.05$.

In the present invention, the results from chitosan-collagen compositions, compared with type-I collagen membrane in the negative control group, showed the ability to enhance new bone formation on titanium implant surface. The present invention further demonstrated heterotopic (extraskeletal) de novo bone formation induced by chitosan-collagen composition around titanium implants in the subcutaneous region of rats. This result demonstrated the osteoinductive potential of chitosan-collagen composition in vivo. In the in-vivo experiment of the present invention, chitosan-collagen composition was shown to be an osteoinductive material based on the following evidence: (i) the formation of calcified structures was verified by whole mount stain with Alizarin red; (ii) the histomorphological tissue profile of the osseous structure was characterized by Toluidine blue staining; and (iii) osteoblast-secreted proteins, osteopontin and alkaline phosphatase, were identified by immunohistochemical staining.

Chitosan may be acting not only as a scaffold material, but may also involve in inducing new bone formation. The osteoinduction is the process of transforming local undifferentiated cells into bone-forming cells. In the present invention, chitosan was dissolved and absorbed onto a collagen membrane. It was able to stimulate ectopic bone formation in a subcutaneous region, similar to the effect of rhBMP2 (recombinant human bone morphogenic protein 2), which is a notable osteoinductive substance and has been used in tissue analysis of subcutaneous or intramuscular implantation in animal models. Therefore, the term osteoinduction was used in the present invention. It has been postulated that chitosan can bind to fibroblast growth factors with its N-acetylglucosamine and therefore stimulate angiogenesis and osteoblast-like cell proliferation. It is our hypothesis that chitosan can attract platelets and other osteoprogenitor cells from circulating blood in surrounding tissues. The subsequent activation of platelets in the graft sites promotes the release of platelet-derived growth factor, such as insulin-like growth factor (IGF), transforming growth factor-$\beta$ (TGF-$\beta$), platelet-derived growth factor (PDGF) and endothelial cell growth factor (ECGF), which are valuable for new bone formation. This in turn activates the cascade of wound healing and osteogenesis. It is possible that heterotopic bone formation involves differentiation of local mesenchymal cells in connective tissue into bone-forming cells under the influence of platelets and related growth hormones, is enhanced by the presence of chitosan. In addition, collagen is a bioactive polymer, but did not induce any detectable ectopic bone formation by itself as the negative control in the present invention. In the present invention, titanium implants have been used as vehicles to carry the chitosan-collagen compositions because of the excellent mechanical properties and the bone compatibility of titanium.

In the present invention, it was shown that, at the sixth week, there was no sign of chondrogenesis after induction by chitosan-collagen composition. This might suggest that chitosan of different molecular weights carried by collagen induced new bone formation via a nonchondrogenic ossification process, possibly similar to the intrinsic osteoinduction mechanism of the porous hydroxyapatite.

Chitosan used in the present invention is a nontoxic, nonimmunoreactive material that would be resorbed at a rate commensurate with new bone formation within a few weeks. Likewise, the full resorption time for the collagen membrane used is about six weeks. In the present invention, it was evaluated whether different molecular weights of chitosan in the chitosan material may lead to different rates of bone formation. The histomorphometric analysis showed that the bone parameters in the 750 kDa chitosan-collagen composition test group were slightly higher than those in the 450 kDa test group. However, the differences were not statistically significant. This indicated that, with regard to new bone formation, the degree of deacetylation of chitosan rather than the molecular weight played a crucial role in cell morphology and activities of osteoblasts in vitro.

The results of the present invention showed that the method might be capable of inducing new bone formation in the subcutaneous tissue. All the molecular weights, either 450 kDa or 750 kDa, of chitosan were effective. Therefore, the method of the present invention might be applied in the future to enhance bone formation and osseointegration of implants, wherein the osseointegration refers to a slow process of growth and adhesion of human bone cells onto the surface of tooth implants.

What is claimed is:

1. A method of treating bone defects in a subject, comprising administrating to the subject an effective amount of a chitosan material, wherein the chitosan material consists of a deacetylated chitosan, a pharmacologically acceptable carrier, an antibacterial agent, a local anesthetic, and an epithelial growth factor, the deacetylated chitosan has a deacetylation degree of 70%~90%, is 0.15% by weight of the chitosan material, and is absorbed in a collagen membrane, and wherein the chitosan material induces heterotopic bone-forming around an implant.

2. The method according to claim 1, wherein the deacetylated chitosan has a molecular weight from 100 kDa to 1,000 kDa.

* * * * *